United States Patent [19]
Allen et al.

[11] Patent Number: 5,476,094
[45] Date of Patent: * Dec. 19, 1995

[54] ACRYLIC COPOLYMER MEMBRANES FOR BIOSENSORS

[75] Inventors: Douglas J. Allen, Indianapolis, Ind.; Robert S. Nevin, Albuquerque, N.M.

[73] Assignee: Eli Lilly and Company, Indianapolis, Ind.

[*] Notice: The portion of the term of this patent subsequent to Feb. 8, 2011, has been disclaimed.

[21] Appl. No.: 152,185

[22] Filed: Nov. 15, 1993

Related U.S. Application Data

[62] Division of Ser. No. 834,002, Feb. 11, 1992, Pat. No. 5,284,140.

[51] Int. Cl.$^6$ .................................................. A61B 5/00
[52] U.S. Cl. .......................................... 128/634; 204/415
[58] Field of Search ................................... 128/632–636, 128/637; 204/403, 415, 153.1, 153.12, 153.16–153.17

[56] References Cited

U.S. PATENT DOCUMENTS

| | | |
|---|---|---|
| 3,220,960 | 11/1965 | Wichterle et al. |
| 3,912,614 | 10/1975 | Spracklen |
| 4,484,987 | 11/1984 | Gough |
| 4,759,828 | 7/1988 | Young et al. |
| 4,890,620 | 1/1990 | Gough |
| 5,030,333 | 7/1991 | Clark, Jr. |
| 5,284,140 | 2/1994 | Allen et al. .......................... 128/634 |

FOREIGN PATENT DOCUMENTS

| | | |
|---|---|---|
| 68509 | 1/1983 | European Pat. Off. |
| 309214 | 3/1989 | European Pat. Off. |

OTHER PUBLICATIONS

*Chemical Abstracts*, No. 177559u, vol. 101 (1984).
*Chemical Abstracts*, No. 177697r, vol. 106 (1987).
*Chemical Abstracts*, No. 223332p, vol. 107 (1987).

M. Kumakura and I. Kaetsu, "Physical Characterization and Molecular Structure of Hydrophilic Polymers Obtained by Radiation Cast–Polymerization of Methoxypolyethylene Glycol Methacrylate Monomers for Biomedical Applications," *J. Mater Sci.*, 18(8), 2430–6 (1983).

S. Gernet, et al., "Fabrication and Characterization of a Planar Electrochemical Cell and Its Application as a Glucose Sensor" *Sensors and Actuators*, 18, 59–70 (1989).

M. Shichiri, "Glycaemic Control in Pancreatectomized Dogs With a Wearable Artificial Endocrine Pancreas," *Diabetologia*, 24, 179–184 (1983).

M. E. Collison and M. E. Meyerhoff, "Chemical Sensors for Bedside Monitoring of Critically Ill Patients," *Analytical Chemistry*, 62, No. 7, 435–437 (1990).

P. Vadgama, "Biosensors: Adaptation for Practical Use," *Sensors and Actuators*, B1, Nos. 1–6, 1–7 (1990).

E. Wilkins and W. Radford, "Biomaterials for Implanted Closed Loop Insulin Delivery System," *Biosensors & Bioelectronics*, 5, No. 3, 167–213 (1990).

A. P. F. Turner and J. C. Pickup, "Diabetes Mellitus: Biosensors for Research and Management," *Biosensors*, 1, 85–115 (1985).

M. Shichiri, et al., "In Vivo Characteristics of Needle–Type Glucose Sensor—Measurements of Subcutaneous Glucose (List continued on next page.)

*Primary Examiner*—Angela D. Sykes
*Attorney, Agent, or Firm*—Woodard, Emhardt, Naughton, Moriarty & McNett

[57] ABSTRACT

Homogeneous membranes are disclosed which are composed of acrylic copolymers and are capable of absorbing 10% to 50% of their dry weight of water. The copolymers include a hydrophilic component which comprises acrylic esters having a poly(ethylene oxide) substituent as part of the alcohol moiety. The copolymers further comprise methacrylate and/or acrylate monomer units. The membranes are useful in the fabrication of biosensors, e.g., a glucose sensor, intended for in vivo use. Variations in the ratios of the monomeric components make possible the fabrication of membranes which have varying permeabilities.

31 Claims, 1 Drawing Sheet

OTHER PUBLICATIONS

Concentrations in Human Volunteers"—*Horm. Metab. Res., Suppl. Ser.,* 20:17–20 (1988).

J. Bruckel, et al., "In Vivo Measurement of Subcutaneous Glucose Concentrations with an Enzymatic Glucose Sensor and a Wick Method," *Klin. Wochenschr.,* 67:491–495 (1989).

J. Pickup, et al., "In Vivo Molecular Sensing in Diabetes Mellitus: An Implantable Glucose Sensor with Direct Electron Transfer," *Diabetologia,* 32:213–217, (1989).

ACRYLIC COPOLYMER MEMBRANES FOR BIOSENSORS

This application is a division of U.S. patent application Ser. No. 07/834,002, filed Feb. 11, 1992, now U.S. Pat. No. 5,284,140.

BACKGROUND OF THE INVENTION

1. Field of the Invention

This invention relates to homogeneous membranes composed of acrylic copolymers that are useful in the fabrication of biosensors intended for in vitro use, particularly glucose sensors.

2. Background of the Invention

Monitoring of many physiological parameters of medical significance is performed in clinical chemistry laboratories which are remote from the patient. Because of the time delay involved, the information obtained is historical and may not reflect the current state of the patient. As a consequence, many researchers are attempting to develop biosensors to be used in vivo which would provide real time data for a number of analytes of clinical importance. An excellent summary of current research in this area has been published by Collison and Meyerhoff (*Analytical Chemistry*, 62, 425–437, 1990).

A primary requirement of such sensors is that they be compatible with the body. At a minimum, the materials used to fabricate the sensor must not exert any toxic or allergic effects on the body. In addition, sensors intended to be used in contact with blood must not provoke a thrombotic reaction. Few polymer materials can meet the stringent requirements of medical applications. Vadgama (*Sensors and Actuators*B1, Nos. 1-6, 1-7, 1990) has summarized the problems involved with interfacing a biosensor with the biological environment.

A second requirement for biosensors intended for in vivo use is that the sensing element must exist in a stable environment. If the environment that the sensing element is exposed to is constantly changing, the sensor will experience "drift", and the values returned by the sensor will be in error. Thus, the sensing element must be "protected" in some way from the harsh biological environment. This is generally accomplished by interfacing a membrane between the sensing element and its environment. Such membranes must be biocompatible or the reaction of the body, e.g., thrombosis or an inflammatory reaction, will result in a continuing perturbation of the environment to which the sensing element is exposed. Thus, biocompatibility of membranes used in the fabrication of biosensors is necessary not only for reasons of safety, but also in order for the sensor to function at all. Wilkins and Radford (*Biosensors & Bioelectronics*, 5, No. 3, 167–213, 1990) have examined these issues for several biomaterials.

A final requirement, obviously, is that the sensor must accurately measure the analyte of interest. The sensing element is potentially exposed to body proteins, electrolytes, medication being administered to the patient, etc., any or all of which may interfere with the measurement. Membranes, then, must not only be biocompatible, but they must allow for accurate detection of the analyte of interest in the presence of a number of chemical entities. Thus, permeability properties must be matched to the design of the sensor as well as the analyte being measured.

Considerable research is currently being directed toward the development of an in vivo glucose sensor. Such a sensor would make it possible to continuously monitor a patient's blood glucose levels and allow the physician to develop therapy tailored to the individual. Most research in this area is devoted to the development of electroenzymatic sensors. Such sensors are simpler and less expensive to fabricate than optical sensors. One problem that must be overcome with such sensors is the requirement that the sensing element have access to a sufficient supply of oxygen. The operational principle of these sensors is based on a reaction between glucose and oxygen. Since the concentration of glucose in the body is much greater than that of oxygen, the local supply of oxygen can become depleted unless some provision is made to control the reaction. These issues have been reviewed by Turner and Pickup (*Biosensors*, 1, 85–115, 1985).

The most favored configuration to date for an electrochemical glucose sensor involves the use of one or two enzymes to catalyze the reaction between glucose and another molecule in order to generate an electrical signal. Typically, glucose oxidase is used to catalyze the reaction between glucose and oxygen to yield gluconic acid and hydrogen peroxide, as follows:

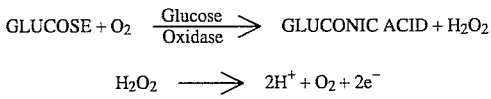

$$H_2O_2 \longrightarrow 2H^+ + O_2 + 2e^-$$

The hydrogen peroxide generated may be detected directly or it may be decomposed by a second enzyme, catalase, in which case the sensor will measure oxygen consumption by the reaction involving glucose oxidase.

A desirable feature of a membrane that will be used for glucose sensors is the ratio of oxygen to glucose diffusion constants. It is not enough to have a membrane which has a high oxygen diffusion constant. Silicone has the highest permeability to oxygen of any polymer, but it is useless as a membrane for glucose sensors because it is completely impermeable to glucose. Other membranes might have good permeability to oxygen but too much permeability to glucose. Thus, an ideal polymer system to be used for fabrication of members for a glucose sensor should allow for the preparation of membranes with varying ratios of the diffusion constants so as to be able to match the properties of the membrane to the particular requirements of the sensor.

There remains a need for polymers which can be fabricated into membranes which meet the above requirements and which can have varying diffusion ratios so that the membrane can be tailored to the specific requirements of the sensor.

SUMMARY OF THE INVENTION

The membranes of the present invention possess unique attributes that satisfy the above objectives. Their properties can be varied to tailor their diffusion characteristics to match the requirements of a particular configuration of a biosensor. The homogeneous membranes of the invention are prepared from biologically acceptable copolymers whose hydrophobic/hydrophilic balance can be varied over a wide range. The membranes are particularly useful in the construction of electrochemical glucose sensors intended for in vivo use.

The membranes of the invention are fabricated from an acrylic copolymer composed of two or more acrylic esters, one of which contains a poly(ethylene oxide) substituent as part of the alcohol moiety. The preferred acrylic copolymers so produced have a water pickup of from about 10% to about 50% of their dry weight of water. By appropriate selection of the reaction components, membranes can be made from these copolymers that can be used to fabricate biosensors intended for in vivo use.

The permeability characteristics of these membranes can be varied over a wide range, making possible their use with a variety of biosensors which depend on the ability of the sensing element to accurately detect a specific analyte. For example, ratios of the diffusion coefficients of oxygen to glucose of up to about 4000, particularly with ratios of about 2500 to about 3500, are preferred for membranes used with an in vivo glucose sensor.

These copolymers are soluble in a variety of solvents and solvent combinations, and thus can be readily fabricated into membranes of various shapes. The membranes of the invention show good adhesion to substrates in an aqueous environment and possess excellent wet-strength. A further advantage of the copolymers from which the membranes of the invention are fabricated is that they exhibit reduced toxicity in biological systems, a key requirement for an implantable sensor of any type.

Further and related objects and advantages of the present invention will be apparent from the following description.

DESCRIPTION OF THE PREFERRED EMBODIMENTS

Figure 1:
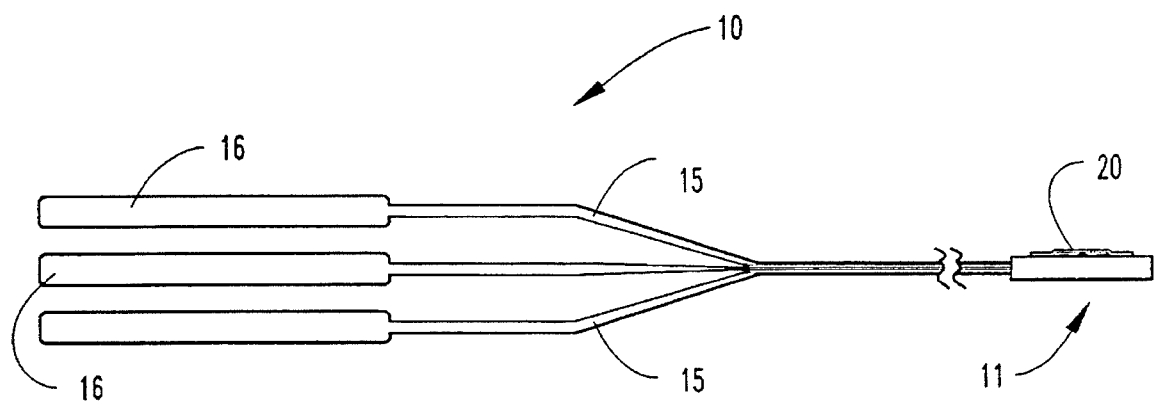
FIG. 1 is a schematic view of a glucose sensor having sensor elements with an acrylic copolymer membrane of the present invention secured thereover.
Figure 2:
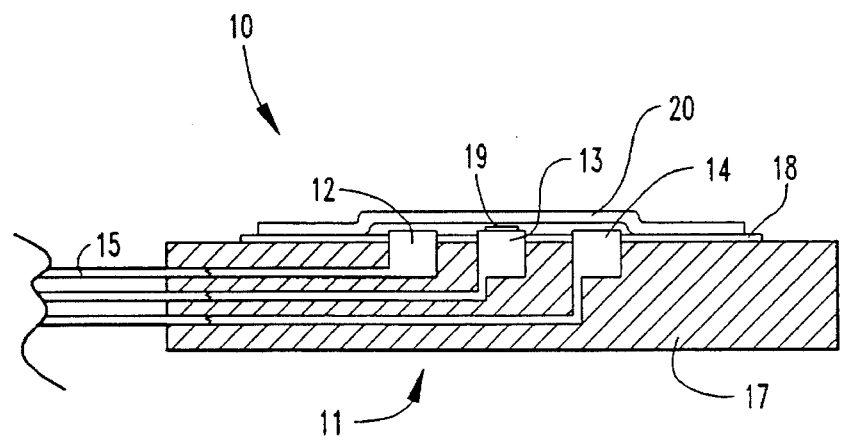
FIG. 2 shows in schematic form an implantable portion of a glucose sensor, with the sensing elements covered with an acrylic copolymer membrane of the present invention.

For the purposes of promoting an understanding of the principles of the invention, reference will now be made to the preferred embodiments and specific language will be used to describe the same. It will nevertheless be understood that no limitation of the scope of the invention is thereby intended, such alterations and further modifications in the preferred embodiments, and such further applications of the principles of the invention as illustrated thereby being contemplated as would normally occur to one skilled in the art to which the invention relates.

The present invention provides acrylic copolymer membranes for use in covering or encapsulating a biosensor, e.g., a glucose sensor, particularly one intended for in vivo use. It has been discovered that the use of such membranes provides many advantages including control of diffusion of the analytes/reactants to the sensor elements to permit accurate analysis, protection of the sensor from the hostile in vivo environment, and biocompatibility.

The membranes of the present invention are prepared by conventional methods by the copolymerization of two or more acrylic ester monomers. The copolymers are soluble in solvents such as acetone, and may be formed as a membrane from solution by dip, spray or spin coating.

One of the acrylic ester monomers of the copolymer contains a poly(ethylene oxide), having an average molecular weight of about 200 to about 2000, as the alcohol component of the acrylic ester. This monomer is referred to as the hydrophilic component of the copolymer. Particularly preferred is a poly(ethylene oxide) having an average molecular weight of about 1000. Examples of such monomers are the methoxy poly(ethylene oxide) monomethacrylates.

The other component(s) of the copolymer may be any of a number of acrylic or substituted acrylic esters, especially the methacrylates and acrylates. Particularly preferred are methyl methacrylate alone or in combination with ethyl acrylate. As will be appreciated by those skilled in the art, variations in the choice of such monomers will influence the properties of the membrane, particularly with regard to hydrophilicity and permeability. Selection of the comonomer(s) used in the membranes may be readily determined by those skilled in the art, without undue experimentation, to achieve the desired physical characteristics of the membranes. All other things being equal, monomers may be chosen on the basis of commercial availability, cost, and ease of purification.

EXAMPLE 1

General Polymerization Procedure

Methods for preparing the membranes of the present invention are known in the art. The following procedure provides a typical methodology.

18.75 g of methyl methacrylate, 6.25 g of methoxy poly(ethylene oxide) monomethacrylate (also known as methoxy polyethylene glycol methacrylate) (MW 1000), 50 mg of 2,2'-azobisisobutyronitrile, and 50 ml of ethoxy ethyl acetate were added to a 200 ml pressure bottle containing a magnetic stirring bar. Nitrogen was bubbled through the stirred solution for 15 minutes. The bottle was then sealed and placed in an oil bath maintained at 75° C. The solution viscosity increased with time so that, after three hours, magnetic stirring stopped. After 24 hours, the bottle was removed from the oil bath and allowed to cool to room temperature. The viscous solution was diluted with 50 ml of acetone. The polymer product was precipitated from 1500 ml of hexane, redissolved in 100 ml of acetone and again precipitated from 1500 ml of hexane. The white lump of polymer was soaked for 16 hours in 500 ml of hexane. Finally, the polymer was dried for 16 hours at 50° C. in a vacuum oven to yield 23.8 g of an off-white, brittle, solid mass. Additional representative polymers prepared by the above procedure are listed in Table 1.

TABLE 1

| # | Methyl Methacrylate (g) | Methoxy Poly(ethylene oxide) Monomethacrylate (g) | Ethyl Acrylate (g) |
| --- | --- | --- | --- |
| 1 | 10.65 | 3.75 | 10.65 |
| 2 | 10.00 | 5.00 | 10.00 |
| 3 | 15.00 | 5.00 | 5.00 |
| 4 | 12.50 | 6.25 | 6.25 |
| 5 | 15.00 | 10.00 | |
| 6 | 20.00 | 5.00 | |
| 7 | 18.75 | 6.25 | |
| 8 | 17.50 | 7.50 | |
| 9 | 16.25 | 8.75 | |
| 10 | 12.50 | 10.00 | 2.50 |
| 11 | 13.75 | 8.75 | 2.50 |
| 12 | 15.00 | 7.50 | 2.50 |
| 13 | 16.25 | 6.25 | 2.50 |
| 14 | 17.50 | 5.00 | 2.50 |
| 15 | 12.50 | 7.50 | 5.00 |
| 16 | 13.75 | 6.25 | 5.00 |
| 17 | 15.00 | 5.00 | 5.00 |
| 18 | 16.25 | 3.75 | 5.00 |
| 19 | 13.75 | 3.75 | 7.50 |

TABLE 1-continued

| # | Methyl Methacrylate (g) | Methoxy Poly(ethylene oxide) Monomethacrylate (g) | Ethyl Acrylate (g) |
|---|---|---|---|
| 20 | 12.50 | 5.00 | 7.50 |

EXAMPLE 2

Molecular weight and water pickup were evaluated for selected polymers prepared in Example 1. Water pickup was determined on films 4.5 cm in diameter dried at 50° C. in vacuo, weighed, immersed in deionized water for 24 hours, removed and blotted with filter paper, and weighed. Percent water pickup was determined from the formula:

$$\% \text{ Pickup} = [(W_w - W_d)/W_d] \times 100$$

where $W_w$ is the weight of the swollen film and $W_d$ is the weight of the dry film. The results are set forth in Table 2.

Molecular weights were determined by Gel Permeation Chromatography using a Waters GPC I liquid chromatograph equipped with two Waters Ultrastyragel® Linear columns, Waters Model R401 differential refractometer detector, and Waters Model 730 Data Module. Determinations were run at 25° C. in toluene. Sample size was 250 microliters at a concentration of 0.25% (w/v). Molecular weights were determined by comparing retention times to a standard plot constructed by running a series of nine polystyrene standards under the same conditions. Thus, reported molecular weights, set forth in Table 2, are "peak" molecular weights.

TABLE 2

| NUMBER | MOLECULAR WEIGHT | % WATER PICKUP |
|---|---|---|
| 5 | 115,000 | 63.2 |
| 6 | 105,000 | 7.1 |
| 7 | 100,000 | 16.2 |
| 8 | 105,000 | 27.2 |
| 9 | 100,000 | 37.2 |
| 10 | 110,000 | 78.8 |
| 11 | 115,000 | 56.5 |
| 12 | 105,000 | 35.9 |
| 13 | 96,000 | 22.3 |
| 14 | 105,000 | 12.9 |
| 15 | 105,000 | 58.8 |
| 16 | 130,000 | 35.5 |
| 17 | 125,000 | 19.8 |
| 18 | 110,000 | 12.3 |
| 19 | 135,000 | 20.2 |
| 20 | 180,000 | 32.8 |
| 21 | 270,000 | 59.8 |
| 22 | 125,000 | 8.8 |
| 23 | 140,000 | 110.4 |
| 24 | 170,000 | 15.5 |
| 25 | 235,000 | 31.3 |
| 26 | 125,000 | 59.2 |

EXAMPLE 3

Membranes were prepared by casting films from a suitable solvent onto glass using a Gardner knife (Gardner Labs). The solvent chosen depends on the particular chemical structure of the polymer. Acetone has been the preferred solvent in work completed to date, since it is readily volatile. Other suitable solvents include chloroform, dichloromethane and toluene. After removal of the solvent, the membranes were hydrated with deionized water for 30–60 minutes. They were then removed and transferred to a Mylar* support sheet. Wet film thicknesses were measured with a micrometer before removal from the support.

Diffusion constants were measured in a standard permeability cell (Crown Glass Co., Inc.) maintained at 37.0° C., plus or minus 0.1° C., using Fick's relationship:

$$J = -D \, dC/dx$$

where J is total flux, D is the diffusion constant, and dC/dx is the concentration gradient across the membrane.

Oxygen diffusion constants were determined by securing the membrane with two rubber gaskets between the two halves of a diffusion cell maintained at 37.0° C., plus or minus 0.1° C., and clamping the two halves together. Each side of the cell was filled with phosphate buffered saline. One side was saturated with nitrogen while the other side was saturated with air. A calibrated oxygen sensor (Microelectrodes, Inc.) was placed in the nitrogen side of the cell, and measurements were taken at 5 minute intervals until the system reached equilibrium. Glucose diffusion constants were determined as above, except that one half of the cell was filled with phosphate buffered saline containing 300 mg/dl of glucose. The concentration of glucose in each half of the cell was measured at appropriate intervals using a Cooper Assist Clinical Analyzer. The diffusion constants and ratios for sample polymers of Example 1 are set forth in Table 3.

TABLE 3

| | D(CM2/SEC) × 10$^{-6}$ | | RATIO |
|---|---|---|---|
| POLYMER | OXYGEN | GLUCOSE | Doxygen/Dglucose |
| 2 | 4.09 | 1.19 | 3.44 |
| 3 | 5.10 | 0.04 | 121.14 |
| 6 | 7.06 | 0.63 | 11.15 |
| 7 | 3.55 | 0.01 | 3550 |
| 9 | 3.44 | 0.09 | 40.47 |
| 10 | 4.51 | 0.22 | 20.69 |
| 11 | 5.74 | 1.09 | 5.27 |
| 12 | 5.51 | 0.75 | 7.35 |
| 13 | 4.42 | 0.17 | 26.00 |
| 14 | 5.73 | 0.08 | 69.04 |
| 16 | 6.23 | 0.77 | 8.09 |
| 17 | 6.85 | 0.61 | 11.23 |
| 21 | 5.56 | 0.26 | 21.38 |
| 22 | 5.51 | 1.10 | 5.01 |
| 24 | 5.99 | 360 | 0.02 |
| 26 | 5.65 | 8.90 | 0.63 |
| 27 | 7.10 | 280 | 0.03 |

The acrylic copolymers are effective, for example, in controlling the diffusion of analytes/reactants to a covered biosensor. By way of example, the polymer #7 was coated as an outer membrane on an electroenzymatic glucose sensor. The sensor responded linearly to glucose in the concentration range of 0 to 400 mg/dl. The sensor did not show an oxygen effect even at oxygen levels as low as 2%. Similar results are achieved with the other copolymers of Example 1, as set forth in Table 3.

As demonstrated in the foregoing, the acrylic copolymers and resulting membranes may be readily prepared having a wide range of diffusion constants and water pickup. These formulations demonstrate the ability to vary these parameters over the desired ranges previously described. This control enables one in the art to tailor the membranes to particular biosensors.

EXAMPLE 4

Cytotoxicity testing was carried out on the acrylic copolymers of Example 1 as follows. The test article size used was 64.3 cm² (1.0 grams). A monolayer of L-929 mouse fibroblast cells was grown to confluency and exposed to an extract of the test article prepared by placing the test article in 11 ml of Minimum Essential Medium (Eagle) and Bovine Serum (5%) and extracting at 37° C. for 24 hours. An MEM aliquot was used as a negative control. After exposure to the extract for 72 hours, the cells were examined microscopically for cytotoxic effect. Presence or absence of a confluent monolayer, intracellular granulation, cellular swelling, and crenation and the percentage of cellular lysis were recorded.

IM implantation testing was carried out as follows. The test article size used was 1 mm wide and 10 mm long. Two healthy, adult New Zealand White rabbits weighing not less than 2.5 kg were used as test animals. Four strips of test material were introduced into the right paravertebral muscle of each rabbit. Two strips of negative control plastic were implanted in the left paravertebral muscle of each rabbit. The animals were humanely killed 7 days after implantation and the entire paravertebral muscle on each side of the spinal cord removed. Cross sections of the muscles were made to locate the implants. The tissue surrounding each implant was examined macroscopically.

Hemolysis testing was also carried out on the acrylic copolymers of Example 1. The test article size used was 1.0 grams, cut into small chips. The sample was placed into each of two extracting tubes containing 10 ml of Sodium Chloride Injection. To each tube was added 0.2 ml of human blood previously collected in a vacuum tube containing E.D.T.A. Tubes were inverted gently to mix the contents, then placed in a constant temperature bath at 37° C. for one hour. The blood-saline mixture was then centrifuged for 10 minutes at 2200 RPM. The absorbance of each sample solution was determined spectrophotometrically at 545 nm and compared to that of a positive control (10 ml water and 0.2 ml blood) and a negative control (10 ml Sodium Chloride Injection and 0.2 ml blood) in order to determine the amount of hemoglobin released from ruptured red blood cells.

Results of the foregoing tests are set forth in Table 4.

TABLE 4

| POLYMER | CYTO-TOXIC | HEMO-LYTIC | IM IMPLANTATION |
|---|---|---|---|
| 1 | NO | | NOT SIGNIFICANT |
| 2 | NO | | |
| 3 | NO | | NOT SIGNIFICANT |
| 4 | NO | | |
| 5 | NO | NO | NOT SIGNIFICANT |
| 6 | | NO | NOT SIGNIFICANT |
| 7 | NO | | |
| 10 | NO | NO | |
| 16 | NO | | |
| 17 | NO | | |
| 18 | NO | | |
| 19 | NO | | |
| 20 | NO | | |
| 21 | NO | | |
| 24 | NO | | |
| 25 | NO | | |
| 26 | NO | | |

The copolymers listed in Table 1 encompass a range of monomer compositions of varying molecular weights and water pickups (Table 2), all of which show excellent biocompatibility. The polymers used to fabricate these membranes must not exhibit any toxic or other harmful effects when placed in the body. Table 4 lists the results of assays for cytotoxicity, hemolysis, and irritation due to IM implantation of representative copolymers of the invention. As can be seen from these results, the copolymers exhibit excellent biocompatibility. The capability to vary the composition of the copolymer to achieve certain specific properties, while maintaining biocompatibility, is also a key feature of this invention.

Particularly useful is the capability to moderate the permeability of these membranes toward particular analytes/reactants, e.g., oxygen and glucose. As can be seen from Table 3, representative copolymers of this invention show widely varying ratios of the diffusion constants of oxygen to glucose, depending upon the monomer composition and the water pickup. A major impediment to the development of an in vivo glucose sensor is the "oxygen deficit" problem. This arises from the fact that the concentration of oxygen in the body is much less than that of glucose. As a consequence, a glucose sensor which depends, directly or indirectly, on measuring the change in oxygen concentration as a measure of the glucose concentration can become an oxygen sensor if the local supply of oxygen is depleted. Thus the sensing element must exist in an environment in which it operates as a true glucose sensor. The membranes of this invention can provide such an environment, since they can be tailored to provide optimum permeabilities of glucose and oxygen.

Referring to the drawings, there is shown in schematic form a biosensor 10 of typical construction covered or encapsulated with a membrane fabricated in accordance with the present invention. The specific construction and operation of the sensor 10 do not form a part of the present invention. For purposes of example but not to be limiting, the inventive membranes are described as used with a glucose sensor. Glucose sensors which utilize glucose oxidase to effect a reaction of glucose and oxygen are known in the art, and are within the skill in the art to fabricate. The present invention depends not on the configuration of the biosensor, but rather on the use of the inventive membranes to cover or encapsulate the sensor elements. Therefore, only a brief description of an exemplary sensor is given herein.

The acrylic copolymer membranes of the present invention are useful with a variety of biosensors for which it is advantageous to control diffusion of the analytes/reactants to the sensing elements. Various such biosensors are well known in the art. For example, other sensors for monitoring glucose concentration of diabetics are described in Shichiri, M., Yamasaki, Y., Nao, K., Sekiya, M., Ueda, N.: "In Vivo Characteristics of Needle-Type Glucose Sensor—Measurements of Subcutaneous Glucose Concentrations in Human Volunteers"— Horm. Metab. Res., Suppl. Ser. 20:17–20, 1988; Bruckel, J., Kerner, W., Zier, H., Steinbach, G., Pfeiffer, E.: "In Vivo Measurement of Subcutaneous Glucose Concentrations with an Enzymatic Glucose Sensor and a Wick Method," Klin. Wochenschr. 67:491–495, 1989; and Pickup, J., Shaw, G., Claremont, D.: "In Vivo Molecular Sensing in Diabetes Mellitus: An Implantable Glucose Sensor with Direct Electron Transfer," Diabetologia. 32:213–217, 1989.

Sensor 10 includes a distal portion 11 in which are located sensor elements 12–14 which are connected through leads 15 to contacts 16. Typical sensing elements would be a counter electrode 12, working electrode 13 and reference electrode 14. Contacts 16 are connected with a suitable monitoring device (not shown), which receives signals and translates this information into a determination of the glucose level detected.

In this type of sensor, glucose oxidase is also provided in the area adjacent the sensor elements, and catalyzes the reaction of glucose and oxygen. This, or a subsequent reaction, is monitored by the sensing elements, and a determination of glucose present in the surrounding subcutaneous tissue may thereby be obtained.

In one design, the sensor 10 includes a substrate material 17 comprising an electrical insulator. This substrate is preferably flexible to facilitate patient comfort. The counter, working and reference electrodes 12–14 are positioned on the substrate and isolated from one another by an insulation layer 18 patterned to selectively expose the active regions of the three electrodes. Glucose oxidase 19 is deposited on the working electrode and all three sensor/electrodes are then covered with a membrane 20 of the present invention.

The distal portion of the sensor is implanted subcutaneously into the body, and the proximal portion including contacts 16 remains external of the body. In accordance with the present invention, the implanted sensor elements 12–14 are covered with a membrane 20 of the present invention, which for the case of a glucose sensor is used to control the rate of diffusion of glucose and oxygen from the surrounding body tissue to the area of the sensor elements. Membrane 20 may fully encapsulate the entire distal portion of the sensor or may simply be layered over the sensor elements. The latter approach may be preferable from the standpoint of ease of fabrication.

The membranes of the present invention are readily formulated to optimize the diffusion and water pickup characteristics for use with various biosensors. By way of example, membranes of the present invention having water pickups of about 10%, 30% and 50% have been evaluated for use with an in vivo glucose sensor. In addition, the inventive membranes having oxygen to glucose diffusion ratios of about 1000, 2000 and 3000 perform acceptably in the foregoing circumstances. The foregoing test results demonstrate that the membranes of the present invention satisfy the requirements for use with a variety of biosensors, namely biocompatibility, providing protection for the sensor elements from the biological environment, and being modifiable to provide characteristics of water pickup and permeability for various analytes/reactants to match a given application.

While the invention has been described in the foregoing description, the same is to be considered as illustrative and not restrictive in character, it being understood that only the preferred embodiments have been described and that all changes and modifications that come within the spirit of the invention are desired to be protected.

What is claimed is:

1. A homogeneous membrane adapted for use on a biosensor having sensor elements for evaluating the presence of an analyte, said membrane being for enclosing the sensor elements, said membrane comprising:

an acrylic copolymer including first monomer units consisting of an acrylic ester having a poly(ethylene oxide) substituent as part of the alcohol moiety, and second monomer units selected from methacrylates, acrylates and combinations thereof, said membrane absorbing about 10% to about 50% of its dry weight of water.

2. The membrane of claim 1 in which said second monomer units comprise methyl methacrylate.

3. The membrane of claim 1 in which said second monomer units comprise ethyl acrylate.

4. The membrane of claim 3 in which said second monomer units further comprise methyl methacrylate.

5. The membrane of claim 1 in which said membrane absorbs about 15% to about 25% of its dry weight of water.

6. The membrane of claim 1 in which the poly(ethylene oxide) substituent has an average molecular weight of from about 200 to about 2000.

7. The membrane of claim 6 in which said membrane absorbs about 15% to about 25% of its dry weight of water.

8. The membrane of claim 6 in which the poly(ethylene oxide) substituent has an average molecular weight of about 1000.

9. The membrane of claim 8 in which said poly(ethylene oxide) substituent comprises methoxy poly(ethylene oxide) methacrylate.

10. The membrane of claim 1 in which said membrane is adapted for use on an electrochemical glucose sensor, and in which said membrane has a ratio of its diffusion coefficient for oxygen to its diffusion coefficient for glucose of up to about 4000.

11. The membrane of claim 10 in which said composition absorbs about 15% to about 25% of its dry weight of water.

12. The membrane of claim 10 in which the poly(ethylene oxide) substituent has an average molecular weight of from about 200 to about 2000.

13. The membrane of claim 10 in which the diffusion ratio for said composition is about 2500 to about 3500.

14. The membrane of claim 13 in which said membrane absorbs about 15% to about 25% of its dry weight of water.

15. The membrane of claim 13 in which the poly(ethylene oxide) substituent has an average molecular weight of from about 200 to about 2000.

16. The membrane of claim 15 in which said membrane absorbs about 15% to about 25% of its dry weight of water.

17. In an implantable device for determining the level of an analyte in a body, said device comprising a biosensor having sensor elements for evaluating the presence of the analyte and including a membrane enclosing the sensor elements, said membrane providing biocompatibility, protection of the sensor elements from the surrounding biological environment, and control of diffusion of materials to the sensor elements, the improvement comprising forming said membrane from an acrylic copolymer comprising first monomer units consisting of an acrylic ester having a poly(ethylene oxide) substituent as part of the alcohol moiety, and second monomer units selected from methacrylates, acrylates and combinations thereof, said membrane absorbing about 10% to about 50% of its dry weight of water.

18. The improvement of claim 17 in which said second monomer units comprise methyl methacrylate.

19. The improvement of claim 17 in which said second monomer units comprise ethyl acrylate.

20. The improvement of claim 19 in which said second monomer units further comprise methyl methacrylate.

21. The improvement of claim 17 in which said membrane absorbs about 15% to about 25% of its dry weight of water.

22. The improvement of claim 17 in which the poly(ethylene oxide) substituent has an average molecular weight of from about 200 to about 2000.

23. The improvement of claim 22 in which the poly(ethylene oxide) substituent has an average molecular weight of about 1000.

24. The improvement of claim 17 in which said biosensor is an electrochemical glucose sensor, said membrane controlling the diffusion of oxygen and glucose to the sensor elements, said membrane having a ratio of its diffusion coefficient for oxygen to its diffusion coefficient for glucose of up to about 4000.

25. The membrane of claim 24 in which the diffusion ratio for said composition is about 2500 to about 3500.

26. The membrane of claim 24 in which said composition absorbs about 15% to about 25% of its dry weight of water.

27. The membrane of claim 24 in which the poly(ethylene oxide) substituent has an average molecular weight of from about 200 to about 2000.

28. The membrane of claim 27 in which the poly(ethylene oxide) substituent has an average molecular weight of about 1000.

29. The membrane of claim 24 in which said second monomer units comprise methyl methacrylate.

30. The membrane of claim 24 in which said second monomer units comprise ethyl acrylate.

31. The membrane of claim 30 in which said second monomer units comprise methyl methacrylate.

* * * * *